(12) United States Patent
Fredricks et al.

(10) Patent No.: US 6,604,003 B2
(45) Date of Patent: Aug. 5, 2003

(54) APPARATUS AND METHOD FOR TREATMENT OF AN INTERVERTEBRAL DISC

(75) Inventors: Raymond Fredricks, Nashua, NH (US); John Shanahan, Medford, MA (US)

(73) Assignee: Sherwood Services AG, Shaffhausen (CH)

( * ) Notice: Subject to any disclaimer, the term of this patent is extended or adjusted under 35 U.S.C. 154(b) by 0 days.

(21) Appl. No.: 09/948,409

(22) Filed: Sep. 6, 2001

(65) Prior Publication Data

US 2002/0065541 A1 May 30, 2002

Related U.S. Application Data (60) Provisional application No. 60/230,750, filed on Sep. 7, 2000.

(51) Int. Cl.⁷ ................................ A61F 7/12; A61F 2/00
(52) U.S. Cl. ..................... 607/99; 607/101; 606/27; 606/29
(58) Field of Search .................... 607/96, 98, 99, 607/101, 113, 115–119, 122; 606/41–50, 27–32; 604/95

(56) References Cited

U.S. PATENT DOCUMENTS

| | | |
|---|---|---|
| 4,411,266 A | 10/1983 | Cosman |
| 4,565,200 A | 1/1986 | Cosman |
| 4,907,589 A | 3/1990 | Cosman |
| 4,955,862 A | 9/1990 | Sepetka |
| 4,966,597 A | 10/1990 | Cosman |
| 5,095,915 A | 3/1992 | Engelson |
| 5,122,137 A | 6/1992 | Lennox |
| 5,304,131 A | 4/1994 | Paskar |
| 5,315,996 A | 5/1994 | Lundquist |
| 5,329,923 A | 7/1994 | Lundquist |
| 5,334,145 A | 8/1994 | Lundquist et al. |
| 5,403,311 A | 4/1995 | Abele et al. |
| 5,433,739 A | 7/1995 | Sluijter et al. |
| 5,437,288 A | 8/1995 | Schwartz et al. |
| 5,441,483 A | 8/1995 | Avitall |
| 5,477,856 A | 12/1995 | Lundquist |
| 5,497,785 A | 3/1996 | Viera |

(List continued on next page.)

FOREIGN PATENT DOCUMENTS

| | | |
|---|---|---|
| EP | 0 521 595 B1 | 2/1992 |
| WO | WO 93/04722 | 3/1993 |
| WO | WO 98 17190 | 4/1998 |
| WO | WO 99 34860 | 7/1999 |
| WO | WO 00 25849 | 11/2000 |
| WO | WO 00/71043 A1 | 11/2000 |
| WO | WO 01/26570 A1 | 4/2001 |

*Primary Examiner*—Roy D. Gibson (57) ABSTRACT

A system and method for approaching the intervertebral disc through a percutaneous insertion from the back of a patient for thermal or electromagnetic treatment of an intervertebral disc, includes an elongated probe member having a guidable region adjacent its distal end with an undulating groove defined in its outer surface. The undulating groove is dimensioned to facilitate bending of the guidable region in at least one radial direction of movement relative to a longitudinal axis of the thermal probe. Preferably, the guidable region includes a plurality of undulating grooves, whereby adjacent undulating grooves are longitudinally spaced with respect to each other. The undulating grooves each define a sinusoidal configuration which may be arranged about an undulating axis extending in oblique relation to the longitudinal axis. The guidable region also includes a longitudinally extending backbone which resists bending of the guidable region in a radial direction of movement. The apparatus may also include a cannula to facilitate introduction of the thermal probe into the intervertebral disc. The cannula includes an arcuate end portion dimensioned to arrange the guidable region of the thermal probe at a desired orientation within the annulus fibrosis.

25 Claims, 8 Drawing Sheets

U.S. PATENT DOCUMENTS

| | | |
|---|---|---|
| 5,536,267 A | 7/1996 | Edwards et al. |
| 5,545,193 A | 8/1996 | Fleischman et al. |
| 5,545,200 A | 8/1996 | West et al. |
| 5,571,147 A | 11/1996 | Sluijter et al. |
| 5,573,520 A | 11/1996 | Schwartz et al. |
| 5,656,011 A | 8/1997 | Uihlein et al. |
| 5,728,149 A | 3/1998 | Laske et al. |
| 5,746,701 A | 5/1998 | Noone |
| 5,785,705 A | 7/1998 | Baker |
| 5,833,632 A | 11/1998 | Jacobsen et al. |
| 5,871,523 A | 2/1999 | Fleischman et al. |
| 5,951,546 A | 9/1999 | Lorentzen |
| 5,980,504 A | 11/1999 | Sharkey et al. |
| 5,983,141 A | 11/1999 | Sluijter et al. |
| 6,001,093 A | 12/1999 | Swanson et al. |
| 6,004,279 A | 12/1999 | Crowley et al. |
| 6,007,570 A | 12/1999 | Sharkey et al. |
| 6,048,339 A | 4/2000 | Zirps et al. |
| 6,073,051 A | 6/2000 | Sharkey et al. |
| 6,095,149 A | 8/2000 | Sharkey et al. |
| 6,099,514 A | 8/2000 | Sharkey et al. |
| 6,099,541 A | 8/2000 | Klopotek |
| 6,102,886 A * | 8/2000 | Lundquist et al. ............ 604/22 |
| 6,122,549 A | 9/2000 | Sharkey et al. |
| 6,126,682 A | 10/2000 | Sharkey et al. |
| 6,146,380 A | 11/2000 | Racz et al. |
| 6,161,048 A | 12/2000 | Sluijter et al. |
| 6,258,086 B1 * | 7/2001 | Ashley et al. ................ 606/41 |
| 6,264,650 B1 | 7/2001 | Hovda et al. |

* cited by examiner

FIG_1

FIG_1A

FIG_5

FIG_6

FIG_9

APPARATUS AND METHOD FOR TREATMENT OF AN INTERVERTEBRAL DISC

CROSS REFERENCE TO RELATED APPLICATIONS

The present application is related to and claims priority to U.S. Provisional Application Ser. No. 60/230,750 filed Sep. 7, 2000, the entire contents of which are hereby incorporated by reference.

BACKGROUND

1. Field of the Invention

The present invention relates generally to advances in medical systems and procedures for prolonging and improving human life. More particularly, this invention relates to a method and apparatus for thermally treating the intervertebral disc to relieve pain associated with abnormalities of the disc due to pathology of the disc or interruption of the various neural processes in and around the disc.

2. Description of the Related Art

The use of radiofrequency electrodes for ablation of tissue in the body or for the treatment of pain is known. In a typical application, a radiofrequency probe or a resistive heating probe may be constructed in an elongated, cylindrical configuration and inserted into the body to a target tissue which is to be treated or ablated. In the case of a radiofrequency probe, there may be an exposed conductive tip portion and an insulated portion of the probe. When connected to an external source of radiofrequency power, heating of tissue occurs near the exposed conductive portion of the probe, whereby therapeutic changes in the target tissue near the conductive tip are created by the elevation of temperature of the tissue. Thermal probes can also be made by resistive heating of a portion of the probe so as to heat surrounding tissue by thermal conduction. By reference, the products of Radionics, Inc., located in Burlington, Mass., include commercially available radiofrequency generators and electrode systems of varied configurations. A paper by Cosman, et al, entitled "Theoretical Aspects of Radiofrequency Lesions in the Dorsal Root Entry Zone", *Neurosurgery*, December 1984, Vol. 15, No. 6, pp. 945–950, describes aspects of tissue heating using radiofrequency electrodes and probes.

The use of thermal therapy in and around the spinal column is also known. Heating of an intervertebral disc to relieve pain is described in commonly assigned U.S. Pat. No. 5,433,739 entitled "Method and Apparatus for Heating an Intervertebral Disc for Relief of Back Pain" and in commonly assigned U.S. Pat. No. 5,571,147 entitled "Thermal Dennervation of an Intervertebral Disc for Relief of Back Pain", the contents of each patent being incorporated herein by reference. In these patents, electrodes are described for either radiofrequency or resistive thermal heating of all or a portion of the intervertebral disc. Straight, curved, and flexible-tipped electrodes are described for this purpose.

U.S. Pat. No. 6,007,570 to Sharkey/Oratec Interventions discloses an intervertebral disc apparatus for treatment of the disc. The apparatus includes a catheter having a self-navigating intradiscal section in the form of a conventional helical coil. In use, the intradiscal section is advanced through the nucleus pulposus and is manipulated to navigate within the nucleus along the inner wall of the annulus fibrosis. An energy delivering member incorporated into the apparatus adjacent the intradiscal section supplies energy to treat the disc area.

The apparatus disclosed in Sharkey '570 is subject to several disadvantages which detract from its usefulness in relieving pain associated with an intervertebral disc. For example, navigation of the helical coil of the catheter within the nucleus pulposus requires the support structure to wrap around in an approximately circular fashion from the anterior portion to the posterior portion of the intervertebral disc. This serpentinus path of the support structure is difficult for the surgeon to effectuate. Moreover, the configuration of the helical support structure increases the risk of probe kinking and is deficient in consistently facilitating the prescribed movement within the disc.

It is desirable to treat the posterior or posterior/lateral portion of the intervertebral disc for the indication of mechanical degeneration of the disc and discogenic back pain. Pain can be derived from degeneration or compression of the intervertebral disc in its posterior or posterior/lateral portions. There is some innervation of the intervertebral disc near the surface of the disc and also within its outer portion known as the annulus fibrosis. Mechanical damage such as fissures or cracks within the disc caused by age or mechanical trauma may result in disc innervation which is believed to be associated with painful symptoms.

Accordingly, the present invention is directed to a novel apparatus and method of use which provides for direct and confirmable placement of a thermal or electromagnetic field (EMF) treating element within the posterior/lateral and posterior portions of an intervertebral disc for thermal treatment. The apparatus includes a percutaneously introducable thermal application device having a novel configuration which provides excellent torque transmission and an increased flexure in a specific direction thereby facilitating the advancement of the thermal device within an intervertebral disc and preferably, for example, in the annulus fibrosus between layers of annular tissue.

SUMMARY

The present invention is a novel and improved system and method for approaching the intervertebral disc through a percutaneous insertion from the back of a patient. In one embodiment, the surgical apparatus includes an elongated thermal or electromagnetic field creating probe member having a guidable region adjacent its distal end with an undulating groove defined in its outer surface. The undulating groove is dimensioned to facilitate bending of the guidable region in at least one radial direction preferably, opposed radial directions, of movement relative to a longitudinal axis of the thermal probe. Preferably, the guidable region includes a plurality of undulating grooves, whereby adjacent undulating grooves are longitudinally spaced with respect to each other. The undulating grooves each define a sinusoidal configuration which may be arranged about an undulating axis extending in oblique relation to the longitudinal axis. The guidable region includes a longitudinally extending backbone which facilitates the desired bending of the guidable region.

The apparatus may also include a cannula to facilitate introduction of the thermal probe into the intervertebral disc. The cannula defines a lumen to receive the thermal probe with the thermal probe being advanceable within the lumen. The cannula includes an arcuate end portion dimensioned to arrange the guidable region of the thermal probe at a desired orientation within the intervertebral disc at a target region, for example, within the annulus fibrosis. The cannula may define a penetrating distal end dimensioned to penetrate the intervertebral disc. Impedance measuring means are associated with the cannula to monitor the impedance of tissue adjacent a distal end of the cannula to provide an indication relating to tissue condition or type.

A preferred method for relieving pain associated with an intervertebral disc having a disc nucleus pulposus and an outer annulus fibrosis surrounding the nucleus pulposus is also disclosed. The method includes the steps of introducing a thermal or electromagnetic field (EMF) transmitting element of a probe into the annulus fibrosis of the intervertebral disc and supplying thermal or EMF energy from an appropriate source to the transmitting element to heat the annulus fibrosis adjacent the transmitting element sufficiently to relieve pain associated with the intervertebral disc.

BRIEF DESCRIPTION OF THE DRAWINGS

The features of the apparatus and method of the present invention will become more readily apparent and may be better understood by referring to the following detailed descriptions of illustrative embodiments of the present disclosure, taken in conjunction with the accompanying drawings, wherein.

DETAILED DESCRIPTION OF THE PREFERRED EMBODIMENTS

The apparatus of the present disclosure provides a more precise controlled positioning of a thermal probe in an intervertebral disc targeted for treatment. It will be readily apparent to a person skilled in the art that the apparatus and method of use of the apparatus can be used to treat/destroy body tissues in any body cavity or tissue locations that are accessible by percutaneous or endoscopic catheters or open surgical techniques, and is not limited to the disc area. Application of the device and method in all of these organs and tissues are intended to be included within the scope of this invention.

In the drawings and the following description, the term "proximal", as is traditional, will refer to the end of the apparatus, or component thereof, which is closest to the operator, and the term "distal" will refer to the end of the apparatus, or component thereof, which is more remote from the operator.

Figure 1:
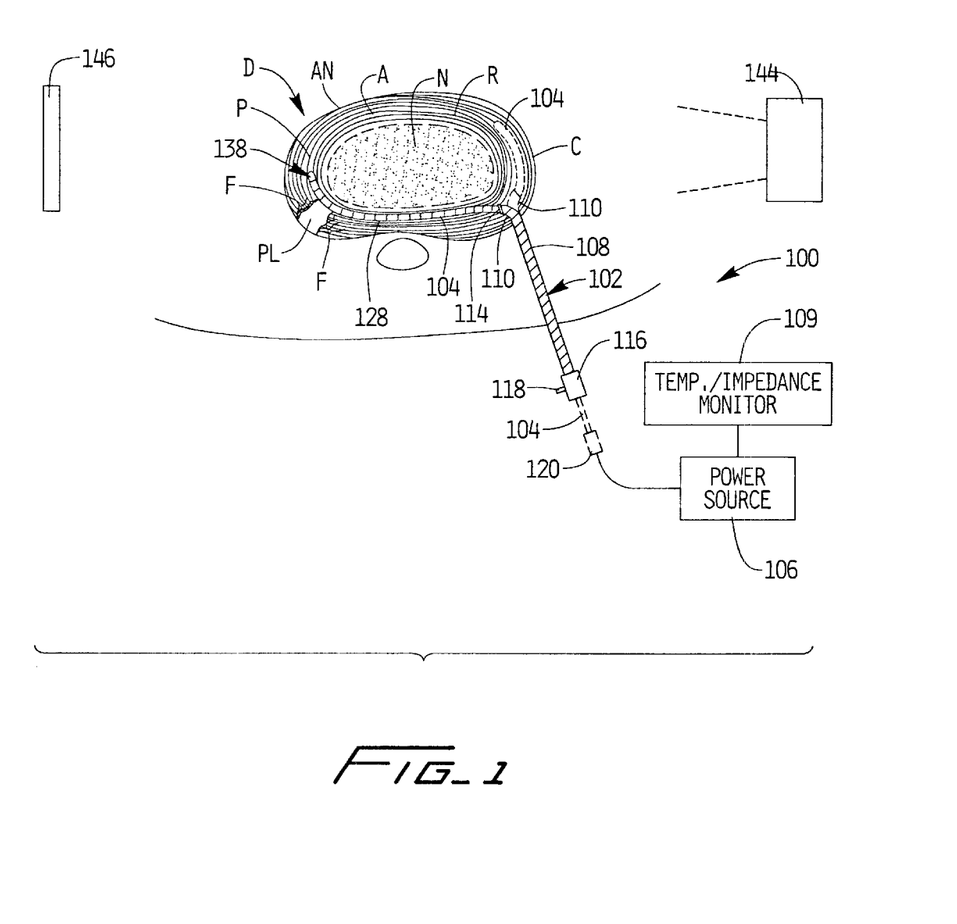
FIG. 1 illustrates the apparatus in accordance with the present invention inserted percutaneously into the annulus fibrosis of an intervertebral disc.

Referring now to FIG. 1, the apparatus of the present disclosure is shown positioned within an intervertebral disc. Prior to a detailed discussion of the apparatus, a brief overview of the anatomy of the intervertebral disc is presented. The intervertebral disc "D" is comprised of an annulus fibrosis "A" and a nucleus pulposus "N" disposed within the annulus fibrosis "A". The annulus fibrosis "A" consists of a tough fibrous material which is arranged to define a plurality of annular cartilaginous rings "R" forming the natural striata of the annulus. The nucleus pulposus "N" consists primarily of an amorphous gel having a softer consistency than the annulus "A". The nucleus pulposus "N" usually contains 70%–90% water by weight and mechanically functions similar to an incompressible hydrostatic material. The juncture or transition area of the annulus fibrosis "A" and nucleus pulposus "N" generally defines, for discussion purposes, an inner wall "W" of the annulus fibrosis "A". The disc cortex "C" surrounds the annulus fibrosis "A". The posterior, anterior and lateral aspects of the intervertebral disc are identified as "P", "AN" and "L", respectively, with the opposed posterior-lateral aspects identified as "PL".

When mechanical stress is put upon a disc or when a disc degenerates with age, fissures, illustrated by the cracks "F" in the drawings, may occur in the posterior or posterior/lateral portions of the disc "D". Problems with the nerves, fissures "F" and degenerative discs can give rise to various patient problems, such as back or leg pain originating from the irritation or occurrence of these abnormalities. Moreover, these conditions may ultimately result in conditions such as bulging or herniated discs. Applicants have realized that heating and/or electromagnetic field (EMF) therapy of the intervertebral disc, preferably, the annulus "A" in the posterior "P" or posterior-lateral "PL" portions, will result in denervation of nerves and/or alterations and thermal ablation of disc structures, which will in turn produce alleviation of pain and healing of the disc. Thus, it is desirable, as shown in FIG. 1, to have a practical method of placing a thermal or electromagnetic probe in the posterior "P" and/or posterior-lateral "PL" portion of a disc "D" where these neural and aberrant structures occur for the relief of pain and other disc related problems.

Figure 2:
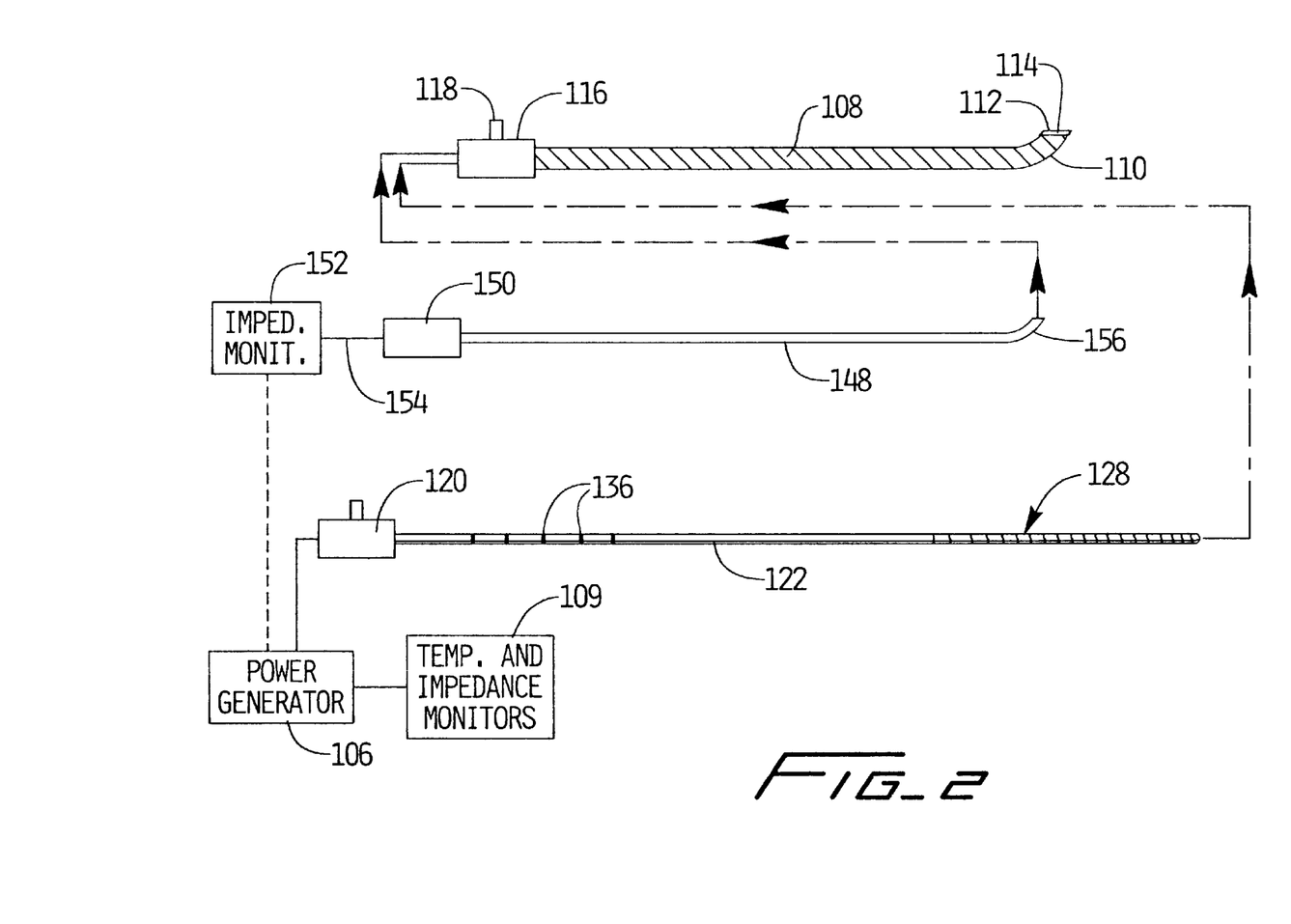
FIG. 2 is a schematic view of the apparatus in a disassembled condition illustrating an insertion cannula, a thermal or EMF probe and associated auxiliary electronic components.

The apparatus of the present invention will now be described. Referring now to FIGS. 1 and 2, apparatus 100 includes outer insertion or introducer cannula 102, thermal or EMF probe 104 which is positionable within the cannula 102 and power source 106 which is connected to the thermal probe 102. Introducer cannula 102 preferably includes a rigid tubular shaft 108 defining a longitudinal axis "a" and having a rigid curved or arcuate portion 110 adjacent its distal end, angularly offset with respect to the longitudinal axis "a" at an angle ranging from about 15 to about 45°, preferably, about 23°. Shaft 108 is preferably composed of a conductive material such as stainless steel or other suitable composition and is insulated with insulation along most of its length as indicated by the hatching in FIGS. 1 and 2. Alternatively, shaft 108 may be fabricated from a suitable polymeric material and formed by conventional injection molding techniques. The distal end portion 112 of shaft 108 may be left uninsulated or exposed to permit electrical connection (e.g., for impedance measuring, etc.) to or contact with the tissue as cannula 102 is placed in the tissue. Alternatively, exposed portion 112 may be connected to power source 106 to heat stimulate or micro-thermal generate the tissue to facilitate passage through the tissue. The extreme distal tip 114 of shaft 108 is preferably sharpened to facilitate penetration into the disc tissue, i.e., through the bone of the cortex "C" and into the annulus "A". A handle or housing 116 is connected to the proximal end of cannula shaft 108 to facilitate manipulation of cannula 102. Handle 116 may include an index marker 118 to indicate the direction of arcuate portion 110 of cannula 102 such that when thermal or EMF probe 104 is introduced within cannula 102, the surgeon may determine in which azimuthal rotational direction the curve is oriented. By reference, exemplary electrode shafts and insulation materials are illustrated by the electrodes manufactured by Radionics, Inc., Burlington, Mass.

Cannula shaft 108 may have a diameter ranging from a fraction of a millimeter to several millimeters and a length of a few centimeters up to about 20 centimeters or more. Alternatively, cannula shaft 108 may be fabricated from an MRI compatible material, including cobalt alloys, titanium, copper, nitinol, etc. Arcuate portion 110 of cannula 102 may assume a variety of angular orientations depending on the surgical procedure to be performed. In one preferred embodiment for thermal or EMF therapy of the intervertebral disc, arcuate portion 110 is arranged such that thermal or EMF probe 104 is generally delivered from cannula 102 in orthogonal relation to longitudinal axis "a".

Power source or generator 106 may be, for example, a radiofrequency generator providing energy at frequencies between several kilohertz to several hundred megahertz. An example of a suitable generator is the lesion generator, Model RFG-3C, available from Radionics, Inc., Burlington, Mass. Power source 106 may have a power output ranging from several watts to several hundred watts, depending on clinical need. Power source 106 may have control devices to increase or modulate power output as well as readout and display devices to monitor energy parameters such as voltage, current, power, frequency, temperature impedance 109, etc., as appreciated by one skilled in the art. Other types of power sources are also contemplated, e.g., including resistive heating units, laser sources, or microwave generators.

Referring now to FIGS. 3–6, in conjunction with FIGS. 1 and 2, thermal or EMF probe 104 of apparatus 100 will be discussed. Thermal or EMF probe 104 is positionable within cannula 102 and is adapted for reciprocal longitudinal movement therewithin. Preferably, EMF probe 104 is a monopolar system and is used in conjunction with an extended surface area grounding pad which contacts the patient's skin over a very large surface area relative the exposed surface area of the electrode tip. Thermal or EMF probe 104 includes handle 120 and elongated member 122 extending distally from the handle 120. Handle 120 is advantageously dimensioned for gripping engagement by the user and may be fabricated from a suitable polymeric material or compatible metal. Handle 120 houses the necessary electrical connectors for connecting to the external power source sensors, etc. Handle 120 may have a visual indicator, e.g., defining a flattened surface 121, to indicate the direction of the elongated member 122. Elongated member 122 defines a longitudinal axis "e" as best illustrated in FIG. 4B, and has an exterior wall 124 defining axial bore or lumen 126, (FIG. 5), extending substantially along its length within the exterior wall. The exterior wall 124 at the proximal end of elongated member 122 is solid or continuous. The distal end of the elongated member includes guidable region 128.

Figure 4A:
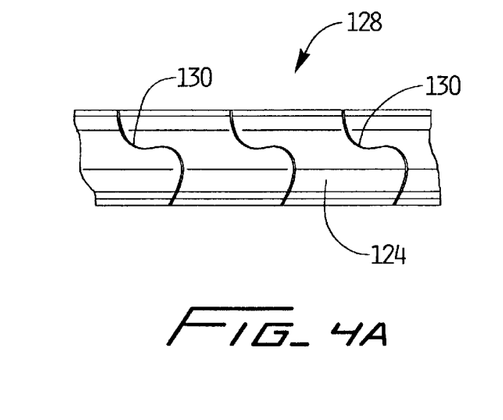
FIGS. 4A and 4B are enlarged views of the guidable region of the thermal or EMF probe illustrating the undulating cuts to facilitate bending movement of the guidable region in a predetermined direction.
Figure 4B:
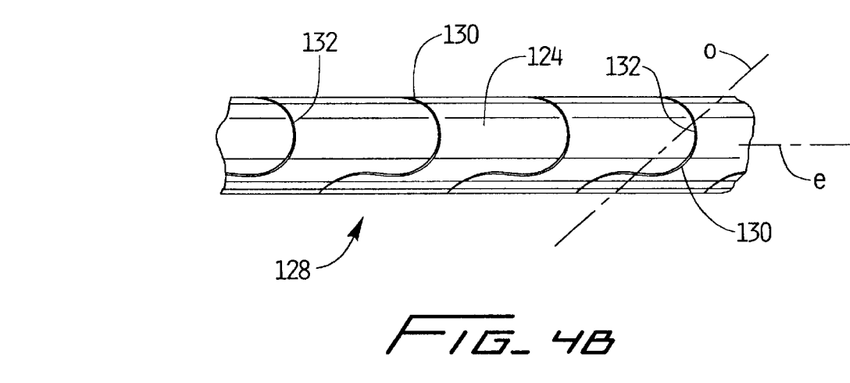
Figure 5:
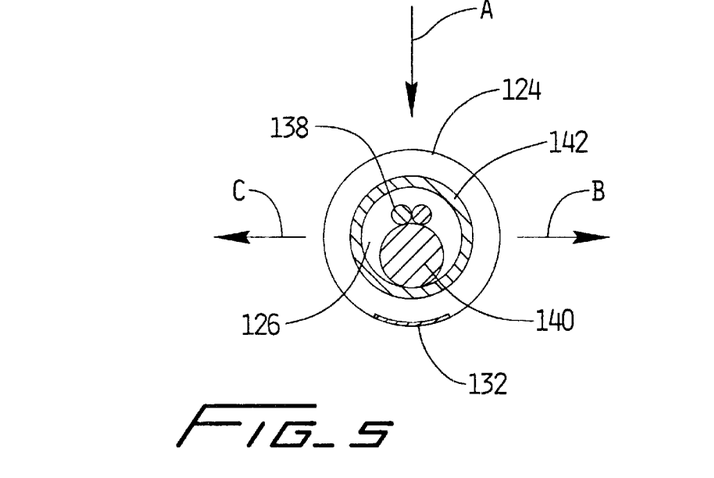
FIG. 5 is a side cross-sectional view of the guidable region of the EMF probe.

As best depicted in the enlarged plan views of a portion of guidable region 128 of FIGS. 4A and 4B and the cross-sectional view of FIG. 5, guidable region 128 has a plurality of interrupted undulating grooves 130 defined in exterior wall 124 and spaced along the longitudinal axis "e" of the probe 104. Grooves 130 preferably define a generally sinusoidal or "s" configuration having a waveform arranged to oscillate about an axis "o" (FIG. 4B) extending in oblique relation to the axis "e" of the probe 104. Grooves 130 extend about the circumference of guidable region 128 and preferably extend radially inwardly to communicate with internal lumen 126 of probe 104 (FIGS. 5 and 6), although, it is envisioned that grooves 130 may terminate within the exterior wall 124 of probe 104 without communicating with the internal lumen 126.

Grooves 130 extend through a radial arc of approximately about 270° to about 350° with respect to the longitudinal axis "e". Grooves 130 are interrupted by backbone 132 (FIG. 4B) which extends the length of guidable region 128. In a preferred method of manufacture, each groove 130 is cut within the exterior wall 124 a predetermined distance to leave a solid portion between the ends of the cuts thereby forming the single backbone 132. Backbone 132 is dimensioned to resist radial arcing movement of guidable region 128 toward the backbone while permitting guidable region 128 to move in radial directions "A, B" (FIGS. 6 and 7) across the backbone 132. Such feature provides significant advantages during positioning of guidable region 128 within the intervertebral disc, including ease of control and guidance into predetermined locations within the disc annulus "a". More specifically, the undulating groove arrangement of guidable region 128 permits the region 128 to bend or flex in opposed radial directions "A" and "B" along one radial plane to follow the ring like configuration of the natural striata of the annulus fibrosis "A" while also providing excellent torque transmission. The undulating groove arrangement also provides a more streamline profile which, consequently, facilitates passage of the probe 104 through the annular tissue, as compared to conventional helical coil arrangements which are subject to "catching" tissue during passage. As depicted in FIG. 7, guidable region 128 may have a preset bend at an angle ranging from about 15° to about 45°, preferably, about 30° relative to the longitudinal axis "e" of the probe 104. A preset bend facilitates introduction of the probe 104 through the curved cannula into the annular tissue "A" to assist in initial guiding of the probe as it exits the cannula along the curved path between annulus tissue layers. Preferably, flattened surface 121 of handle 120 is aligned with the bend to indicate to the user the orientation of guidable region 128.

As will be appreciated, backbone 132 also serves as a more direct electrical pathway from the energy source to the distal end portion of probe 104 and, therefore, advantageously reduces the electrical resistance of guidable region 128 thereby facilitating uniform lesion formation along the length of the exposed electrode tip. The distal tip 134 of guidable region 128 is preferably blunt or rounded to prevent undesired entry or penetration of thermal probe into areas, including underlying nerves, the nucleus pulposus, etc., as will be discussed. The proximal end of thermal or EMF probe 104 includes a plurality of etchings or markings 136 (FIG. 2). Markings 136 indicate the degree of extension of guidable region 128 from cannula 102.

When used as a radiofrequency probe, thermal or EMF probe 104 may be insulated except for guidable region 128 which may be left uninsulated for transmission of energy. Alternately, and in the preferred embodiment, thermal or EMF probe 104 may be uninsulated while cannula 102 functions as the insulating element of the apparatus. In this arrangement, the degree of extension of guidable region 128 beyond cannula 102 determines the heating capability of the probe 104.

Figure 6:
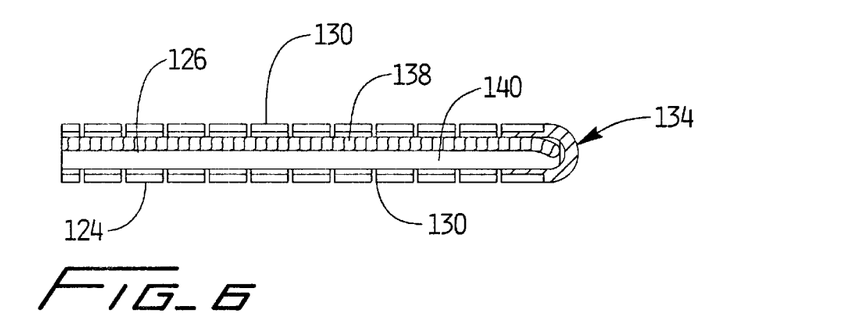
FIG. 6 is a cross-sectional view of the guidable region taken along the lines 6—6 of FIG. 3.
Figure 7:
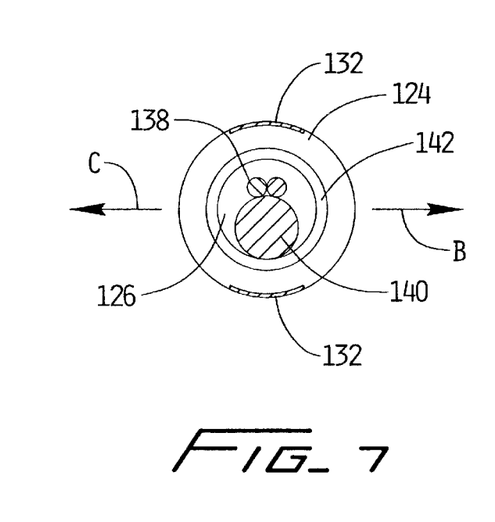
FIG. 7 is a perspective view illustrating the pre-bend configuration of the guidable region of the EMF probe.

With reference to FIGS. 5–6, thermal or EMF probe 104 may further include a thermal sensor 138, e.g., a thermocouple, thermistor, etc., extending through its internal lumen 126. Sensor 138 is preferably embedded in solder tip 139 which also closes the distal tip 134 of probe 104. Thermal sensor 138 provides temperature monitoring capability of the tissue being treated adjacent thermal or EMF probe 104 through temperature monitor 109. (FIGS. 1 and 6)

Figure 3:
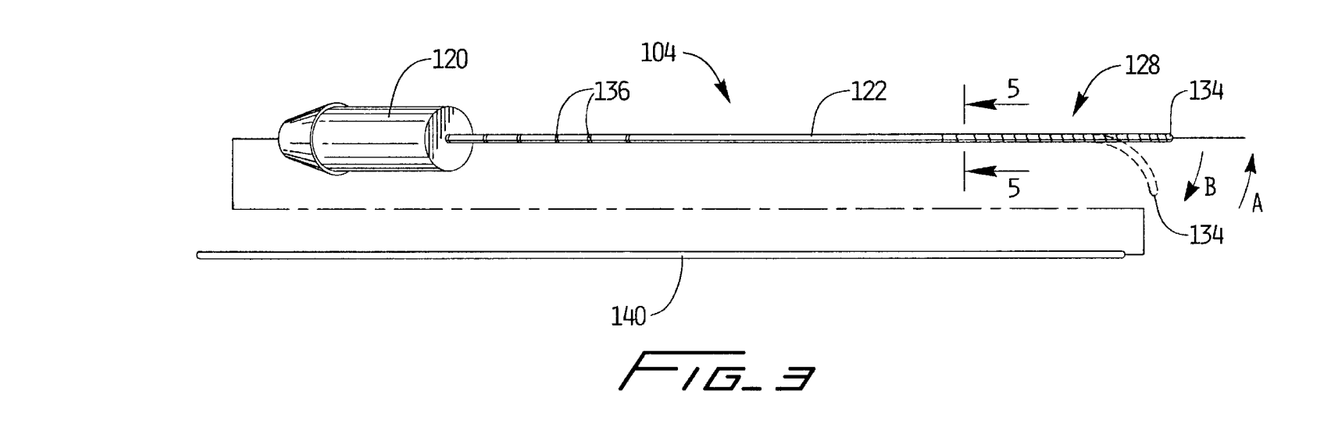
FIG. 3 is a perspective view of the thermal probe of the apparatus.

Referring particularly to FIGS. 3, 5 and 6, thermal or EMF probe 104 further includes a guide wire 140. Guide wire 140 is disposed within internal lumen 128 of thermal or EMF probe 104. Guide wire 140 has sufficient rigidity to assist in advancing thermal or EMF probe 104 with annulus "A" while also permitting guidable region 128 of the probe 104 to flex and bend to conform to the path defined by the natural striata of the fibrous annulus tissue. Guide wire 140 is also embedded in solder tip 139 at the distal end of probe 104. In a preferred arrangement, thermosensor 138 is wrapped about the distal end of guide wire 140 and embedded in the solder tip 139.

Figure 8:
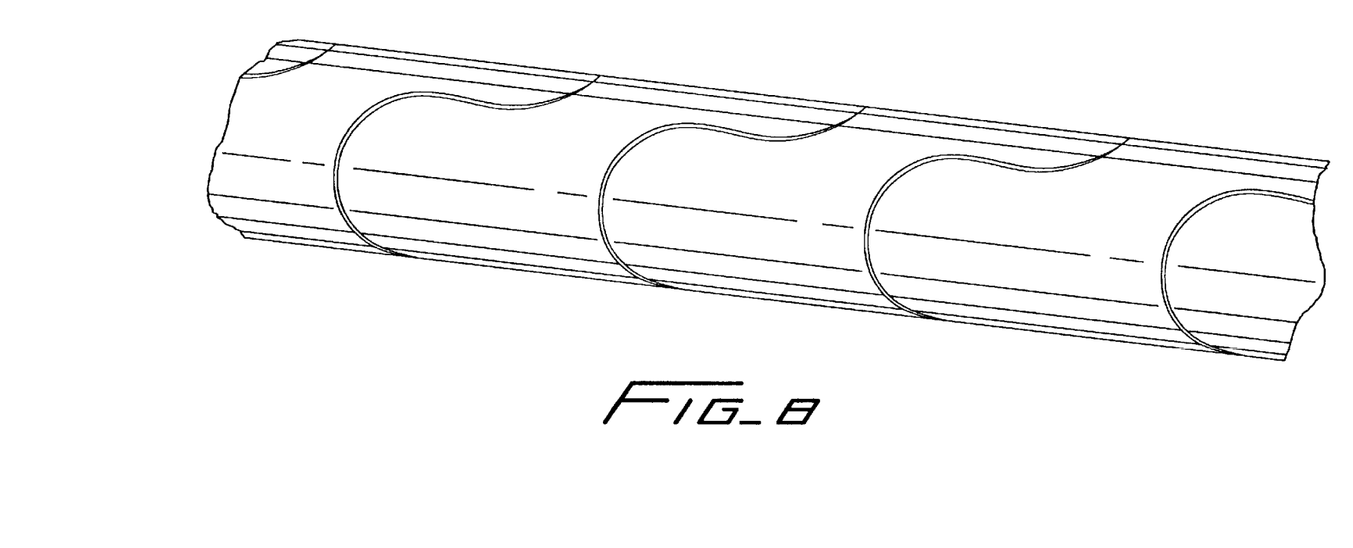
FIG. 8 is a side plan view of the proximal end of the EMF probe illustrating auxiliary electrical components associated with the probe.
Figure 9:
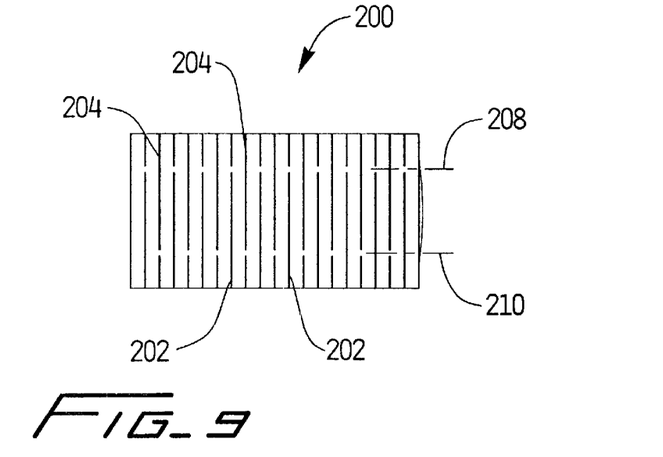
FIG. 9 is a side cross-sectional view of the handle and associated electrical connections of the probe.
Figure 10:
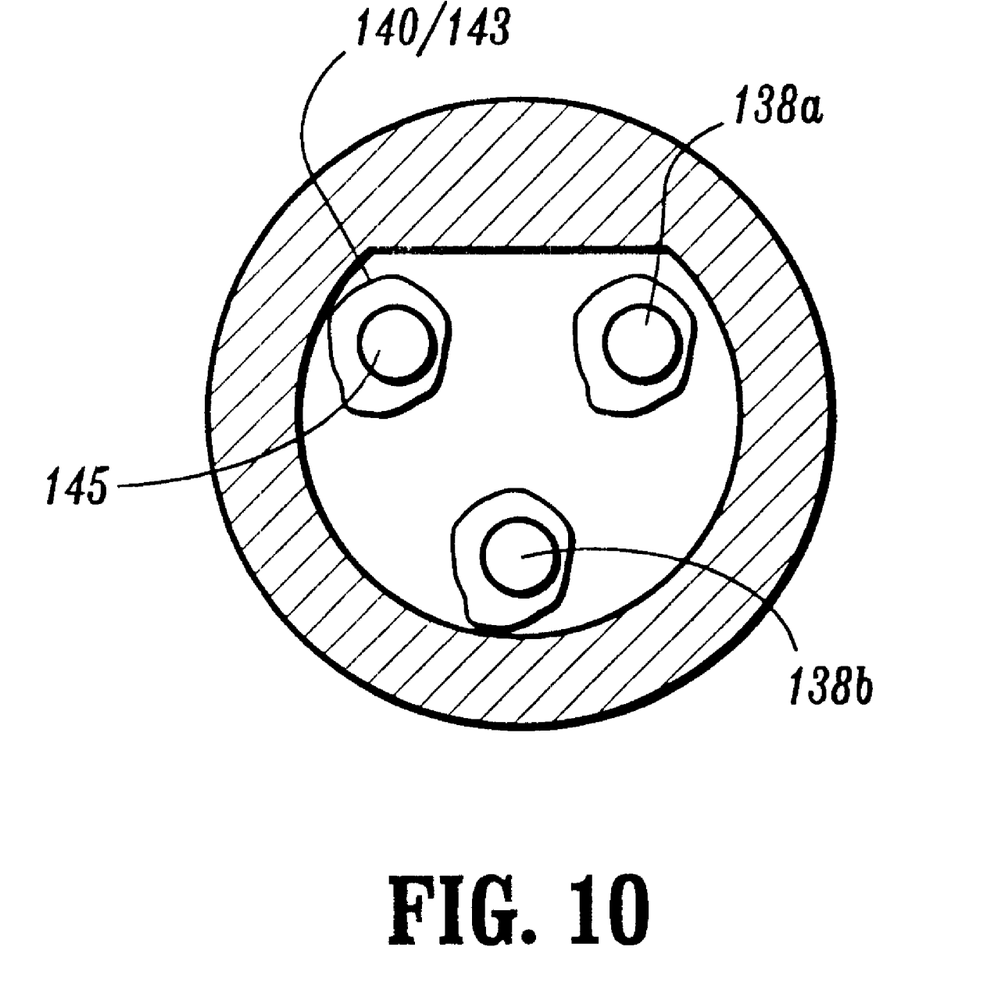
FIG. 10 is a cross-sectional view of the handle further illustrating of respective electrical components of the probe.

With reference to FIGS. 8–10, in view of FIG. 5, guide wire 140 serves to carry electrical signals with elongated member 122 of probe 104 to the distal end of the probe 104. Specifically, guide wire 140 and elongated member 122 are electrically connected to each other at their respective proximal ends through wire 143 (e.g. a #26 BUSS wire) which is soldered to the proximal end of the elongated member 122. Wire 143 and guide wire 140 are connected to an RF energy input pin 145 of handle 102. (shown schematically in FIG. 8). This construction provides parallel dual pathways for the RF energy: 1) through elongated tubular member 122 of probe 104 originating from the proximal end thereof and traveling distally; and 2) through guide wire 140 to the distal end 134 of probe 104. This dual path structure energy transmission provides a significant advantage in that it facilitates a more uniform application of RF energy along the entire length of the exposed distal end of EMF probe 104. The remaining connectors of handle 102 include pins 138a, 138b for connection to respective constantan and copper wires of the thermocouple 138.

In an alternative embodiment, only elongated member 122 is connected to the RF energy input with the guide wire 140 being electrically isolated from the tube.

As depicted in the cross-sectional views of FIGS. 5 and 6, thermal or EMF probe 104 may further include flexible sleeve 142 which encloses thermal sensor 138 and guide wire 140. Sleeve 142 serves to maintain the alignment of thermal sensor 138 and guide wire 140 within thermal or EMF probe 104 and also prevents or minimizes entry of body fluids within the probe 104. Sleeve 142 preferably comprises a flexible polymer material, such as polyimide.

With reference again to FIGS. 1 and 2, the remaining components of the apparatus will be discussed. Apparatus 100 preferably includes an imaging system 144 to potentially monitor, control or verify the positioning of cannula 102 and/or thermal probe 104. Imaging systems contemplated include X-ray machines, fluoroscopic machines or an ultrasonic, CT, MRI, PET, or other imaging devices. Several of these devices have conjugate elements as illustrated by element 146 on the opposite portion of the patient's body to provide imaging data. For example, if the imaging machine is an X-ray machine, element 146 may be a detection device, such as an X-ray film, digital, X-ray detector, fluoroscopic device, etc. Use of imaging machines to monitor percutaneously placed electrodes into tissue is commonly practiced in the surgical field.

With continued reference to FIG. 2, in conjunction with FIG. 1, apparatus 100 may further include stylet 148 which is to be used in conjunction with cannula 102. Stylet 148 is positionable within the lumen of cannula 102 and preferably occludes the front opening of the cannula 102 to prevent entry of tissue, fluids, etc., during introduction of the cannula 102 within the intervertebral disc "D". Stylet 148 may include a proximally positioned hub 150 which mates with handle 116 of cannula 102 to lock the components together during insertion. Such locking mechanisms are appreciated by one skilled in the art. An impedance monitor 152 can be connected, as shown by connection 154, to stylet 148 and therefore communicates electrically with the exposed portion 112 of cannula 102 into which the stylet 148 is introduced to monitor impedance of the tissue adjacent the distal end of cannula 102. Alternatively, connection of the impedance monitor may be made directly to the shaft of cannula 102 whereby impedance measurements are effectuated through the exposed distal end of the cannula 102. Once the combination of stylet 148 and cannula 102 are inserted into the body, impedance monitoring assists in determining the position of cannula tip 112 with respect to the patient's skin, the cortex "C" of the disc, the annulus "A", and/or nucleus "NU" of the disc "ID". These regions will have different impedance levels that are readily quantifiable. For example, for a fully insulated electrode or cannula with an exposed area of a few square millimeters at the cannula end, the impedance will change significantly from the position of the tip near to or contacting the cortex "C" of the disc to the region where the tip is within the annulus "A" of FIG. 1 and further where the tip is within the nucleus "NU" of the disc. Differences of impedance can range from a few hundred ohms outside the disc, to 200 to 300 ohms in the annulus, to approximately 100 to 200 ohms in the nucleus. This variation can be detected exquisitely by the surgeon by visualizing impedance on meters or by hearing an audio tone whose frequency is proportional to impedance. Such a tone can be generated by monitor 109 in FIG. 2. In this way, an independent means is provided for detecting placement of the curved cannula within the disc. Thus, e.g., in an application where the EMF probe 104 is to be inserted between adjacent layers of annular tissue, undesired penetration of the EMF probe 104 tip portion 112 of cannula 102 through the inner wall "W" of the annulus "A" and into the nucleus pulposus "N" can be detected via the impedance monitoring means.

Stylet 148 can be made of a rigid metal tubing with either a permanent bend 156 at its distal end to correspond to the curvature of arcuate portion 112 of cannula 102 or may be a straight guide wire to adapt to the curve of the cannula 102 when it is inserted within the cannula 102. The hub 150 and connector 154 can take various forms including luer hubs, plug-in-jack-type connections, integral cables, etc. By reference, example of electrodes and cables are illustrated in the product lines of Radionics, Inc., Burlington, Mass.

Surgical Procedure

The use of the apparatus 100 in accordance with a preferred procedure for thermal treatment of an intervertebral disc will now be discussed. With reference to FIG. 1, the targeted intervertebral disc "D" is identified during a pre-operative phase of the surgery. Access to the intervertebral disc area is then ascertained, preferably, through percutaneous techniques or, less desirably, open surgical techniques. Cannula 102 with stylet 148 positioned and secured therein is introduced within the intervertebral disc "D" preferably from a posterior or posterior-lateral location as depicted in FIG. 1. Alternatively, cannula 102 may be utilized without stylet 148. During introduction of the assembled components, the impedance of the tissue adjacent the distal end 114 of the cannula 102 is monitored through the cannula 102 or alternatively via the impedance monitoring means associated with stylet 148. Impedance monitoring may be utilized to determine the position of cannula tip 114 with respect to the patient's skin, the cortex "C" of the disc, the annulus "A" and/or the nucleus "N" of the disc. As discussed above, these regions have different and quantifiable impedance levels thereby providing an indication to the user of the position of the cannula tip 112 in the tissue. Monitoring of the location of cannula 102 may also be confirmed with imaging system 144. In a preferred procedure, cannula tip 114 of cannula 102 is positioned within the annulus fibrosis "A" of the intervertebral disc "D" at a posterior lateral "PL" location of the disc "D" without penetrating through inner wall "W" and into nucleus "N". As appreciated, sharpened tip 114 facilitates entry into the annulus "A".

Thereafter, cannula 102 is angulated to position arcuate end portion 110 of the cannula 102 at the desired orientation within the annulus fibrosis "A". Confirmation of the angular orientation of arcuate end portion 110 of cannula 102 is made through location of index marker 118 of the cannula 102. In one preferred orientation, arcuate end portion 110 is arranged to deliver thermal probe 104 within the posterior section "P" of the intervertebral disc "D". In an alternative procedure, arcuate end portion 110 is arranged to deliver thermal or EMF probe 104 toward the posterior-lateral "PL" and lateral "L" portion of the disc "D" as shown in phantom in FIG. 1.

Stylet 148 is then removed from cannula 102. Thermal or EMF probe 104 is positioned within the internal lumen of cannula 102 and advanced through the cannula 102. Preferably, the pre-bent orientation of guidable region 128 is arranged to coincide with the arcuate end portion of the cannula 102. Confirmation of this orientation may be made with the location of the flattened surface 121 of the handle 102. The probe 104 is advanced to at least partially expose guidable region 128 of the thermal or EMF probe 104 from the distal end of cannula 102. As thermal or EMF probe 104 enters the annulus fibrosis "A", guidable region 128, due to its strategic configuration and undulating groove 130 arrangement, flexes and conforms to the natural striata of the annular rings "R" of the annulus fibrosis, i.e., follows a path defined by the natural striata between two adjacent annular layers of tissue without entering the nucleus "N". Once positioned, guidable region 128 occupies a substantial portion of the posterior "P" section of the annulus fibrosis "A" and preferably extends to the opposed posterior lateral section "PL" of the annulus fibrosis. The degree of extension of guidable region 128 beyond cannula 102 may be indicated by distance or index markings 136 on the shaft of thermal or EMF probe 104 and confirmed through imaging system 144. In the alternate method shown in phantom in FIG. 1, arcuate end portion 110 is angulated to directly access the posterior lateral "PL" section of the annulus fibrosis "A" also without entering the nucleus pulposus. Thermal or EMF probe 104 is thereafter advanced to position guidable region 128 within the lateral "L" and posterior/lateral "PL" sections of the annulus "A". Similar to the predescribed method of application, guidable region 128 follows the arcuate path of the natural striata of the annulus "A" upon advancement therein. In either method, confirmation of the orientation of arcuate end portion 110 is provided through index pin or marker adjacent handle of the cannula and can be also monitored through imaging system 144.

Figure 1A:
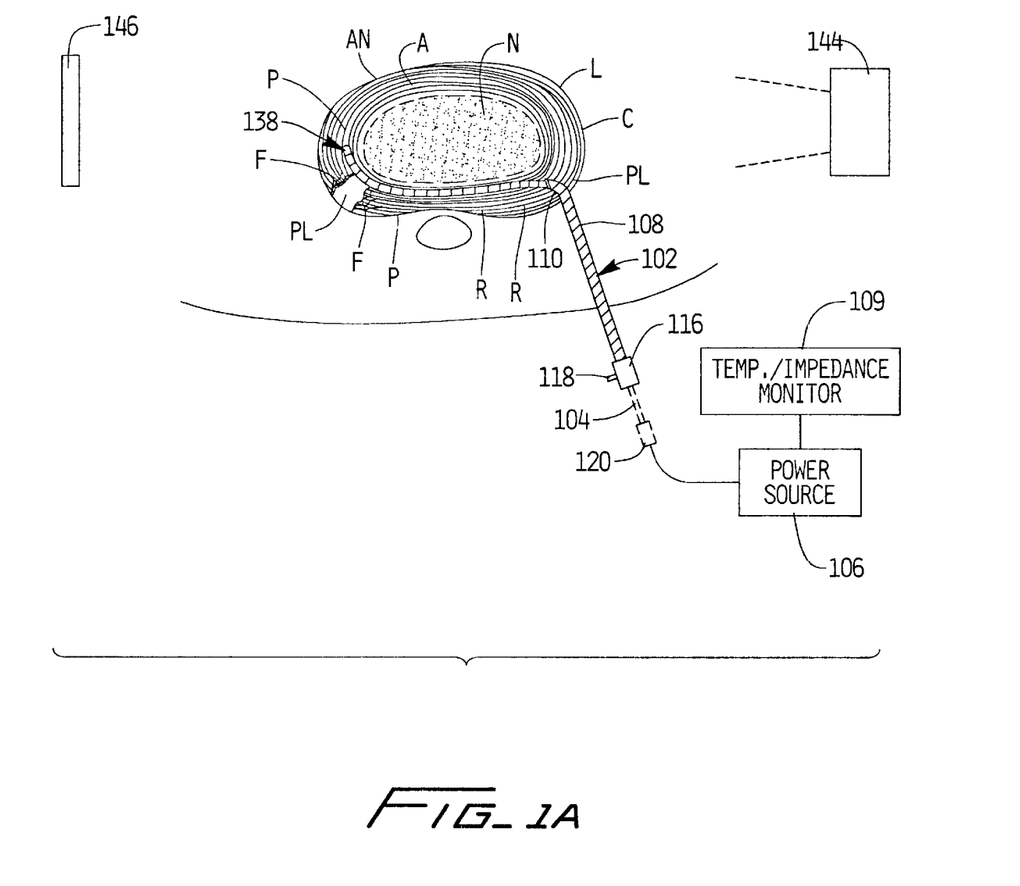
FIG. 1A is a view illustrating an alternate use of the apparatus of FIG. 1.

In one alternative method of application depicted in FIG. 1A, cannula 102 may be positioned adjacent inner wall "W" of annulus. As in the preferred embodiment previously described, thermal or EMF probe 104 is advanced within the annulus fibrosis "A" between adjacent layers, whereby guidable region 128 follows along the arcuate path defined by the adjacent annular tissue layers without penetrating through the wall "W" and into the nucleus "N".

Once the guidable region 128 is positioned within the annulus "A" as desired, the power source 106 is activated whereby the thermal or EMF probe 104 delivers thermal energy and/or creates an electromagnetic field through guidable region 128 adjacent the intervertebral disc "D" to produce the thermal and/or EMF therapy in accordance with the present invention. Appropriate amounts of power, current or thermal heat may be monitored from the external power source 106 and delivered for a certain amount of time as determined appropriate for clinical needs. For example, if denervation of nerves surrounding the disc is the objective, the tissue adjacent the probe end is heated to a temperature of from about 45° to about 60°. If healing of fissures in the disc is the surgical objective, the temperature in the tissue is raised to about 60–75° C. As appreciated, the degree of extension of guidable region 128 from cannula controls the volume of disc tissue heated by the probe 104. Thermal sensor 138 of thermal or EMF probe 104 can provide information concerning the temperature of tissue adjacent the distal end. The impedance means associated with e.g., EMF probe 104, can provide impedance measurements of the tissue thereby providing an indication of the degree of dessication, power rise, or charring, that may be taking place nea the thermal probe tip 134. This indicates the effectiveness of the treatment and guards against unsafe contraindications of the therapy. By reference, use of impedance monitoring in neurosurgery is described in the paper byh E. R. Cosman and B. J. Cosman, entitled "Methods of Making Nervous Syustem Lesions", in Neurosurgery, Vol. 3, pp. 2490–2499, McGraw Hill 1985.

Thus, the apparatus of the present invention provides significant advantages over the prior art.

Cannula 102 and thermal or EMF probe 104 permits the probe to be directed from a location across the posterior margin and into the lateral portion of the disc "D" by a direct pathway along, e.g., the natural striata of the annulus fibrosis or along the inner wall "W" of the annulus fibrosis. This represents a more direct approach to the posterior/lateral portions of the disc than the more circuitous approach involving delivering a probe into the nucleus center of the disc and then arcing the probe around through an anterior or anterior-lateral pathway through the nucleus "N". Moreover, the present invention eliminates the need of known devices to penetrate the inner annulus wall "W" and enter the nucleus "N" with a guide.

A further advantage of the present invention is that by monitoring impedance of cannula 102 and/or thermal or EMF probe 104 as it is being positioned within the disc, the surgeon can get additional information on the positioning of the cannula 102 as it is being put into the proper orientation.

A further advantage of the present invention is that by use of a curved introduction cannula a more efficacious direction of the probe can be achieved in the difficult lumbar or lumbar-sacral intervertebral discs. In these approaches, nearby heavy bony structures, such as the iliac crest, can often obscure a placement of a curved probe parallel to the end plates or bony margins of adjacent intervertebral discs. By appropriate angulation and rotation of a curved cannula, the extension of a thermal probe parallel to the so-called end plates of the intervertebral discs is made possible with minimal repositioning and manipulation of the introduction cannula.

The undulating groove arrangement and backbone of the guidable region of the thermal probe permits flexing in at least opposed radial directions along one radial plane to follow the arcuate path in the intervertebral disc. The undulating groove arrangement also provides a streamline profile thereby facilitating entry and passage through the annulus tissue.

In typical radiofrequency procedures using the apparatus and process of the present invention, power levels of fractions of a watt to several tens of watts may be used depending on the extent of heating required and the degree of therapy, denervation, and disc healing that is desired to be achieved.

A further advantage of the present system and method is that it enables simple, minimally-invasive, percutaneous, out-patient treatment of intradiscal pain without the need for open surgery as for example discectomies or spinal stabilization using plates, screws, and other instrumentation hardware. A further advantage of the present invention is that it is simple to use and relatively economical. Compared to open surgery, the treatment of disc by percutaneous electrode placement represents only a few hours procedure and minimal hospitalization, with minimal morbidity to the patient. Open surgical procedures often require full anesthetic, extensive operating room time, and long hospital and home convalescence. Such open surgeries have considerable risk of morbidity and mortality and are much more expensive than a percutaneous procedure as described in accordance with the present invention.

It is also envisioned that thermal or EMF probe could be, or incorporate, a resistive heating element(s) to heat the disc tissue by resistive heating. For example, within the distal end there may be a resistive wire such as a nichrome wire or other type of resistive element, such that current delivered to the resistive element from the power generator will produce resistive heating within the element. Such heating of the proximate disc material when the electrode is inserted into the disc of a patient. Various construction details for such resistive heating elements can be devised by those skilled in the art. For example, a resistive wire can be fabricated to produce the guidable region. Alternatively, an internal resistive wire can be placed inside the guidable region. The overall shaft may be coated with an insulative material or other material to produce appropriate frictional, thermal, or electrical characteristics of the electrode when it is placed in the disc. Like the high frequency electrode embodiment, as described above, such a resistive element may have the appropriate flexibility, or steering capability so that it can be steered or directed favorably within the appropriate portion of the posterior and posterior-lateral portions of a disc, as illustrated by the discussion associated with FIG. 1 above.

In another configuration of the thermal probe, in accordance with the present disclosure, the distal end may comprise a microwave antenna system or a laser fiber with transducer to distribute energy through thermal element into surrounding disc tissue. In the configuration shown in FIG. 1, the thermal transmitting element operates as a microwave antenna or laser transmitting element, respectively. Other constructions to produce a heating element can be devised by those skilled in the art and are intended to be included within the scope of the present invention. It is further envisioned that the thermal or EMF probe provided with undulating cuts can be positioned such that the transmitting guidable region is disposed within the nucleus "N".

In such an embodiment, however, the probe must be configured and dimensioned so as to be more flexible than that of the previously disclosed embodiment. For example, the probe 104 may have a different diameter, thickness, material of fabrication and/or different arrangement and orientation of the grooves 132. This is so because the probe which is to be inserted into and navigated within the nuclear material must have greater flexibility to prevent puncturing through the opposing side of the nucleus pulposus back into the annulus. Also, the greater flexibility facilitates navigation of the probe along the inner surface of the nucleus. Whereas, in the previously described embodiment, the opposite is desirable. In particular, the probe of the previously described embodiment must be significantly more rigid to provide increased columnar strength to prevent kinking of the probe caused by greater relative resistance encountered by navigating in the annular tissue. The two embodiments would not, therefore, be interchangeable in their methods of use, i.e., operating in the annular tissue as for the previously described embodiment and operating in the nuclear material as for the embodiment of this paragraph.

Figure 11:
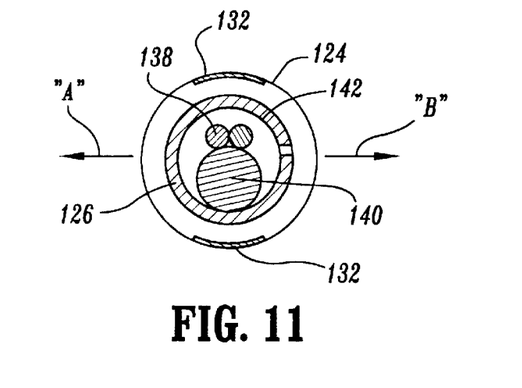
FIG. 11 is a cross-sectional view similar to the view of FIG. 6 and illustrating an alternate embodiment of the EMF probe.

Referring now to the cross-sectional view of FIG. 11, a further alternative embodiment of the probe of the present invention is disclosed. This probe is substantially similar to the probe of the prior embodiment but, includes, a second backbone 132 in diametrical opposed relation to the first backbone 132. Second backbone 132 is created by interrupting the sinusoidal grooves 130 adjacent the area of the second backbone 132. This double backbone arrangement permits radial movement along one plane in directions "A and "B", but, also enhances rigidity of the guidable region, which may be desirable in certain surgical applications.

Referring now to FIG. 11, there is illustrated a further alternative embodiment of the probe of the present invention. This probe is similar to the probe 104 of the first embodiment, but, includes a single continuous sinusoidal groove 170 extending the length of the guidable region 172. This configuration provides for uniform radial movement in all radial directions with respect to the longitudinal axis. Such configuration may be advantageous when inserting probe along a more serpenticious path. Groove 170 extends to communicate with the internal lumen of the probe as discussed hereinabove.

Figure 12:
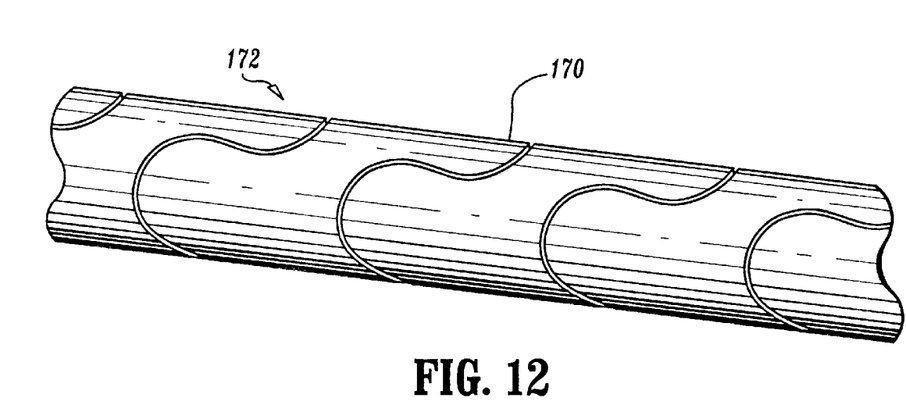
FIG. 12 is a perspective view of a guidable region of another alternate embodiment of the thermal or EMF probe.
Figure 13:
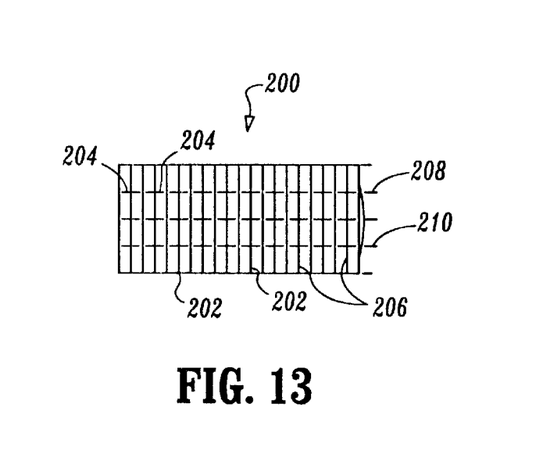
FIG. 13 is a side view of the guidable region of another alternate embodiment of a thermal or EMF probe according to the present disclosure.

Referring now to FIG. 12, there is illustrated another alternative embodiment of thermal or EMF probe 104. Thermal or EMF probe 104 includes a guidable region 200 having a plurality of partial annular grooves 202 or cuts spaced along the longitudinal axis "Z". FIG. 12 is an enlarged plan view of a portion of guidable region 200. In a preferred embodiment, annular grooves 202 radially extend about the exterior wall through an arc which is slightly less than 360°, thereby providing a solid region 204, 206 between the respective starting and ending positions of the groove. Adjacent grooves 202 are radially displaced at about 180°. The overall effect of this arrangement is that guidable region can flex uniformly in all radial directions. This configuration is advantageous in insertion of the probe along a more serpenticious path.

While the above description contains many specific examples, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical apparatus for thermal or electromagnetic treatment of tissue, which comprises:

an elongated thermal probe member having proximal and distal ends and defining a longitudinal axis, the probe member having a guidable region adjacent the distal end, the guidable region having an undulating groove defined in an outer surface thereof and being dimensioned to facilitate bending of the guidable region in at least one radial direction of movement relative to the longitudinal axis, the thermal probe being adapted for connection to a thermal energy source to provide thermal energy to tissue.

2. The surgical apparatus according to claim 1 wherein the guidable region includes a plurality of undulating grooves, adjacent undulating grooves being longitudinally spaced with respect to each other.

3. The surgical apparatus according to claim 2 wherein the undulating grooves each define a sinusoidal configuration.

4. The surgical apparatus according to claim 3 wherein the guidable region includes a longitudinally extending backbone, the backbone being devoid of the undulating grooves and being dimensioned to resist bending of the guidable region in a radial direction of movement.

5. The apparatus according to claim 4, further including impedance measuring means associated with the cannula to monitor the impedance of tissue adjacent a distal end of the cannula to provide an indication relating to tissue condition or type.

6. The surgical apparatus according to claim 2 wherein the probe member defines an internal lumen, the undulating grooves extending to communicate with the internal lumen.

7. The surgical apparatus according to claim 2 including a cannula to facilitate introduction of the thermal probe into the intervertebral disc, the cannula defining a lumen to receive the thermal probe, the thermal probe being advanceable within the lumen.

8. The apparatus according to 7 wherein the cannula includes an arcuate end portion, the arcuate end portion dimensioned to arrange the guidable region of the thermal probe to a desired orientation within the annulus fibrosis.

9. The apparatus according to claim 8 wherein the cannula defines a penetrating distal end dimensioned to penetrate the intervertebral disc.

10. The apparatus according to claim 7 wherein the cannula includes an index marker adjacent a proximal end thereof to indicate a direction of the arcuate end portion.

11. The apparatus according to claim 8 wherein the impedance measuring means includes a stylet positionable within a lumen of the cannula.

12. The surgical apparatus according to claim 1 wherein the one undulating groove is arranged about an undulating axis extending in oblique relation to the longitudinal axis.

13. The apparatus according to claim 2 wherein the thermal transmitting element is a resistive heating element.

14. The apparatus according to claim 2 wherein the thermal transmitting element is a radio-frequency electrode.

15. The apparatus according to claim 2 wherein the thermal transmitting element is a microwave antenna.

16. The apparatus according to claim 1 wherein the thermal transmitting element is a laser transmitting member.

17. The apparatus according to claim 1 including temperature sensing means for sensing temperature of tissue during application of thermal energy.

18. A method for relieving pain associated with an intervertebral disc having a disc nucleus pulposus and an outer annulus fibrosis surrounding the nucleus pulposus, comprising:

providing an elongated thermal probe member having proximal and distal ends and defining a longitudinal axis, and having a flexible guidable region adjacent the distal end, the guidable region having a plurality of spaced undulating grooves defined in an outer surface thereof;

introducing the flexible guidable region of the thermal probe into the annulus fibrosis of the intervertebral whereby the flexible guidable region bends adjacent the undulating grooves to follow a generally arcuate path through the annulus fibrosis without entering the nucleus pulposus; and supplying thermal or electromagnetic energy from an energy source to heat or induce an electromagnetic field adjacent the annulus fibrosis sufficiently to relieve pain associated with the intervertebral disc.

19. The method according to claim 18 wherein the step of introducing includes positioning a thermal transmitting element of the probe adjacent at least one of a posterior section, lateral section and posterior-lateral section of the annulus fibrosis.

20. The method according to claim 19, including the step of accessing the annulus fibrosis from a posterior-lateral section of the intervertebral disc.

21. The method according to claim 20 further including the step of positioning a cannula adjacent the intervertebral disc and passing the thermal probe through a lumen of the cannula into the outer annulus fibrosis.

22. The method according to claim 21 wherein the cannula includes an arcuate portion adjacent a distal end thereof and wherein, during the step of introducing the thermal probe, the arcuate cannula portion guides the flexible probe portion along the path through the annulus fibrosis.

23. The method according to claim 22 wherein the step of positioning includes at least partially introducing the distal end of the cannula into the annulus fibrosis.

24. The method according to claim 23 further including the step of angulating the arcuate portion to a desired orientation within the annulus fibrosis.

25. The method according to claim 19 including the step of monitoring impedance of tissue to detect variations in tissue-type to thereby facilitate positioning of the thermal transmitting element in the annular fibrosis.

* * * * *